United States Patent [19]

Toth

[11] Patent Number: 5,579,359
[45] Date of Patent: Nov. 26, 1996

[54] METHODS AND APPARATUS FOR CALIBRATING DETECTOR CELL OUTPUT SIGNALS

[75] Inventor: Thomas L. Toth, Brookfield, Wis.

[73] Assignee: General Electric Company, Milwaukee, Wis.

[21] Appl. No.: 576,764

[22] Filed: Dec. 21, 1995

[51] Int. Cl.$^6$ .............................. A61B 6/03; G06F 19/00; G06F 159/00
[52] U.S. Cl. ...................... 378/19; 378/901; 364/413.17
[58] Field of Search ..................... 364/413.15, 413.16, 364/413.17; 378/4, 19, 901

[56] References Cited

U.S. PATENT DOCUMENTS

| | | | |
|---|---|---|---|
| 4,812,983 | 3/1989 | Gullberg et al. | 364/413.17 |
| 5,131,021 | 7/1992 | Gard et al. | 378/19 |
| 5,450,461 | 9/1995 | Hsieh | 378/19 |
| 5,473,656 | 12/1995 | Hsieh et al. | 378/4 |

Primary Examiner—P. Porta
Assistant Examiner—David Vernon Bruce
Attorney, Agent, or Firm—John S. Beulick; John H. Pilarski

[57] ABSTRACT

The present invention, in one form, is a method for determining and applying a ZCAL correction vector to the channel outputs from the detector array in a multi-slice CT system. More specifically, and in accordance with one embodiment of the present invention, the signal gain for each detector cell, or channel, at multiple z-axis locations is measured. For each channel, a correction polynomial $Q_n$ is fitted to the signal variation curve as a function of z-axis position so that the correction polynomial value multiplied by its channel signal produces a constant value over the operational range of z-axis positions. Beam positions ($Z_r$) are measured as a function of each position reference signal ($D_r$) and the Z position of the beam at the sensor channel and the location of the focal spot are determined. The z-axis location for each channel and the ZCAL correction vector are then determined. The ZCAL correction vector is then multiplied by the channel signal to calibrate the channel signal.

14 Claims, 3 Drawing Sheets

BEAM ON DETECTOR VS. CHANNEL POSITION

METHODS AND APPARATUS FOR CALIBRATING DETECTOR CELL OUTPUT SIGNALS

FIELD OF THE INVENTION

This invention relates generally to computed tomography (CT) imaging and more particularly, to calibrating x-ray beams in the z-axis in multi-slice CT systems.

BACKGROUND OF THE INVENTION

In at least one known CT system configuration, an X-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the X-ray beam by the object. Each detector element of the array produces a separate electrical signal that is a measurement of the beam attenuation at the detector location. The attenuation measurements from all the detectors are acquired separately to produce a transmission profile.

In known third generation CT systems, the X-ray source and the detector array are rotated with a gantry within the imaging plane and around the object to be imaged so that the angle at which the X-ray beam intersects the object constantly changes. A group of X-ray attenuation measurements, i.e., projection data, from the detector array at one gantry angle is referred to as a "view". A "scan" of the object comprises a set of views made at different gantry angles during one revolution of the X-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

In performing a scan, the effects of thermal, gravitational, and centrifugal forces cause the x-ray source focal spot to move approximately about 0.5 mm in the z (or patient) direction. The emitted x-ray beam pivots about the z-axis collimator, and the 0.5 mm z-axis movement of the focal results in approximately about +/−2 mm beam movement at the detector. Since the detector z-axis sensitivity is not perfectly uniform, particularly at the detector cell edges, such movement of the x-ray beam may cause noticeable ring and band artifacts in a resulting image.

In single slice (i.e., one row of detector cells) imaging systems, the x-ray beam position is determined using a z-axis position sensing channel, sometimes referred to in the art as the Z channel. An attenuating wedge, as is well known in the art, typically is used in connection with the Z-channel.

Calibration data, sometimes referred to as the ZCAL vector, is obtained by measuring the gain of each channel, or detector cell, and the corresponding beam location on the Z-channel, for two z-axis positions. The two z-axis positions are typically about 1 mm apart. A cold X-ray tube scan is used for one z-axis position and a hot X-ray tube scan is used for the other z-axis position. A ZCAL correction vector is then generated to represent the slope of the gain difference for the gains sensed at the two z-axis positions for each channel in accordance with the above described condition, i.e., cold and hot x-ray tube scans.

Just prior to performing a scan, an air calibration (or "fastcal") is performed. Specifically, for a fastcal and subsequent to warmup of the x-ray tube, the mean channel gains are measured for each detector cell with the x-ray beam at one beam location. The one beam location is identified by the Z-channel. The gains in the vicinity of the beam location expected during most clinical operation rather than at the cold position extreme. The ZCAL correction vector is normalized based on the measured mean gains and during patient scanning, each channel gain is adjusted by the ZCAL correction vector according to the expected gain change associated with the distance that the beam moved, as determined by the Z-channel, from its position at the time of fastcal.

In a two slice imaging system, the x-ray detector typically includes two rows of detector cells arranged adjacent to each other in the z-axis direction. Specifically, edges of detector cells in one row are adjacent edges of detector cells in the other row.

In operation, the x-ray beam typically impinges on the x-ray detector at the location of the adjacent detector cell edges. The sensitivity of each detector cell, as is known in the art, typically is non-linear at the detector cell edge region. Therefore, the detector cell gain variation will also be non-linear.

To eliminate the detector cell non-linearity, a precision post-patient collimator may be used to form the z-axis x-ray beam profile so that only the x-ray beam umbra falls on the detector cells. Z axis movement of the focal spot does not change the x-ray intensity on the detector thereby avoiding differential signal errors and associated artifacts. Of course, the penumbra and some margin amount of the umbra are unused in such a configuration. Even though such portions of the x-ray beam are unused, the patient is still exposed to the x-ray dose required to generate such unused x-ray beam portions to avoid the imaging problems associated with the x-ray beam penumbra on the detector cell edge regions.

To reduce dose, some of the x-ray beam penumbra can be allowed to impinge on the detector. Good ZCAL correction, however, is required under such conditions. Although it would be desirable to reduce the patient dose by eliminating the post patient collimator, the ZCAL correction vector described above in connection with single slice imaging systems does not adequately calibrate detector signals due to x-ray beam movement over the non-linear detector cell regions. Therefore, and in order to reduce patient dose, there is a need for a ZCAL correction vector which takes into account detector cell edge region non-linearities so that calibrated attenuation data can be obtained in a multi-slice imaging system. It also would be desirable to eliminate the costly precision post-patient collimators in a multi-slice imaging system.

SUMMARY OF THE INVENTION

These and other objects may be attained in a system which, in one embodiment, determines and applies a ZCAL correction vector to the channel outputs from the detector array in a multi-slice CT system. More specifically, and in accordance with one embodiment of the present invention, the signal gain for each detector cell, or channel, at multiple z-axis locations is measured. For each channel, a correction polynomial $Q_n$ is fitted to the signal variation curve as a function of z-axis position so that the correction polynomial value multiplied by its channel signal produces a constant value over the operational range of z-axis positions. Beam positions ($Z_r$) are measured as a function of each position reference signal ($D_r$) and the Z position of the beam at the sensor channel and the location of the focal spot are determined. The z-axis location for each channel and the ZCAL correction vector are then determined. The ZCAL correction vector is then multiplied by the channel signal to calibrate the channel signal.

The ZCAL correction vector described above can be used to calibrate channel signals in a multi-slice imaging systems, even in the presence of non-linearities due to the detector cell edge regions. Use of such ZCAL correction vector also eliminates use of;costly precision post-patient collimators in a multi-slice imaging system.

DETAILED DESCRIPTION OF THE DRAWINGS

Figure 1:
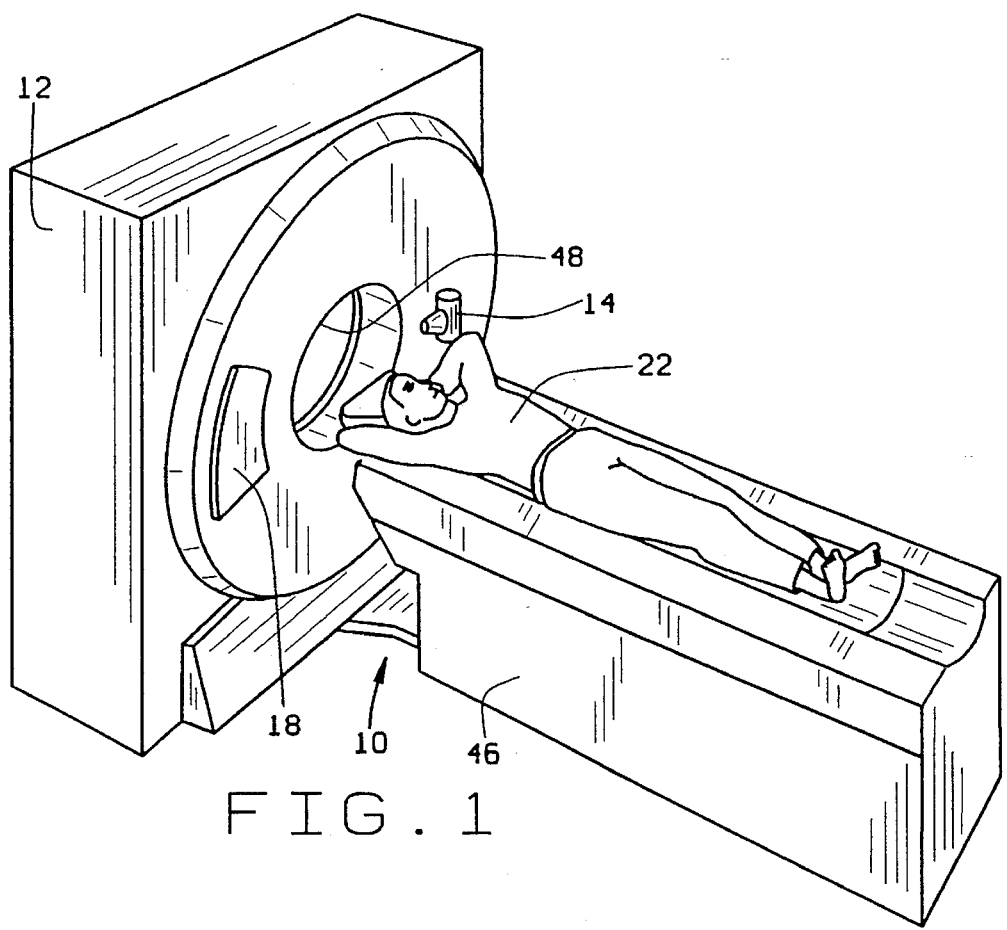
FIG. 1 is a pictorial view of a CT imaging system.
Figure 2:
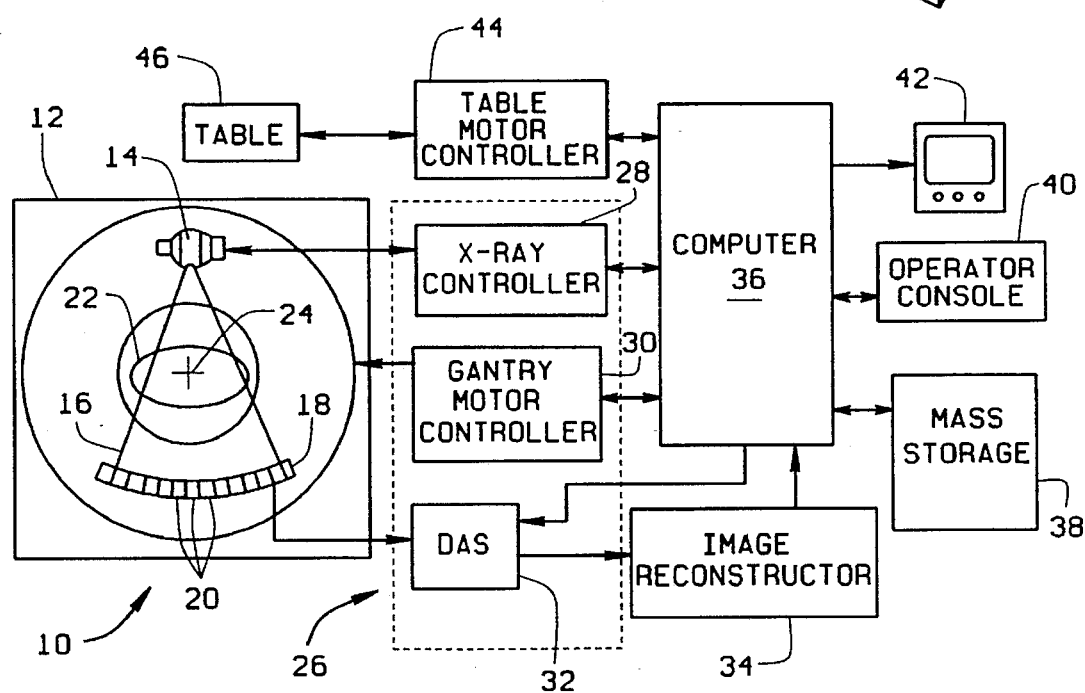
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an X-ray source 14 that projects a beam of X-rays 16 toward a detector array 18 on the opposite side of gantry 12. Detector array 18 is formed by detector elements 20 which together sense the projected X-rays that pass through a medical patient 22. Each detector element 20 produces an electrical signal that represents the intensity of an impinging X-ray beam and hence the attenuation of the X-ray beam as it passes through patient 22. During a scan to acquire X-ray projection data, gantry 12 and the components mounted thereon rotate about a center of rotation 24.

Rotation of gantry 12 and the operation of X-ray source 14 are governed by a control mechanism 26 of CT system 10. Control mechanism 26 includes an X-ray controller 28 that provides power and timing signals to X-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized X-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, X-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
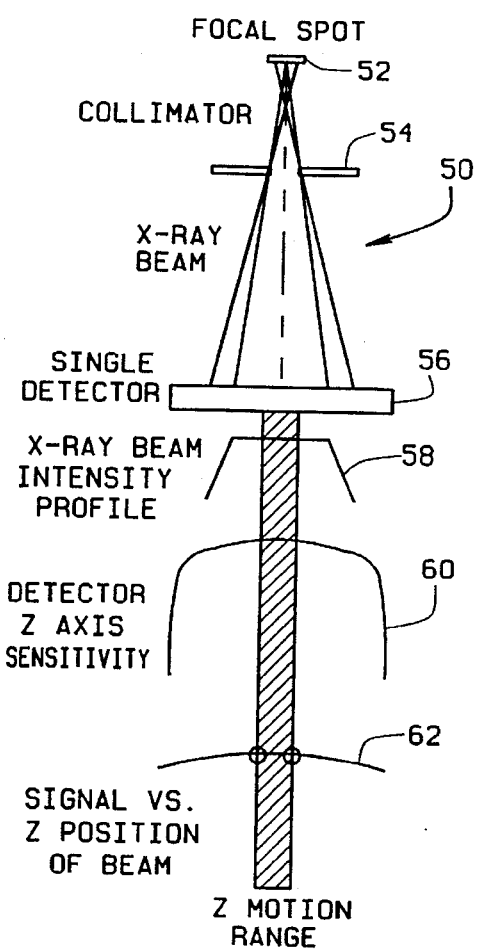
FIG. 3 schematically illustrates an x-ray beam and a detector cell, including the x-ray beam intensity profile, the detector cell z axis sensitivity, and the detector cell signal versus z axis position of the x-ray beam.

FIG. 3 illustrates a single slice (i.e., one row of detector cells) imaging system 50 including an x-ray being emitted from a focal spot 52. The x-ray is collimated by a prepatient collimator 54 and impinges on a surface of a detector cell 56. An x-ray beam intensity profile 58 and a detector cell z axis sensitivity curve 60 are graphically shown below cell 56. In addition, a detector cell signal versus z axis position of the x-ray beam curve 60 also is shown.

With single slice imaging system 50, calibration of the output from cell 54 can be performed in a straightforward manner based on the z-axis location of the beam on the surface of cell 54. Specifically, the gain can be measured for two spaced beam positions on the surface of detector 54, and from such data, the ZCAL correction vector can be generated. Since the gain on most of the surface of detector 54 is substantially uniform, and since the beam moves in the z-axis only about 0.5 mm, the ZCAL correction vector provides acceptable calibration in a single slice system.

Figure 4:
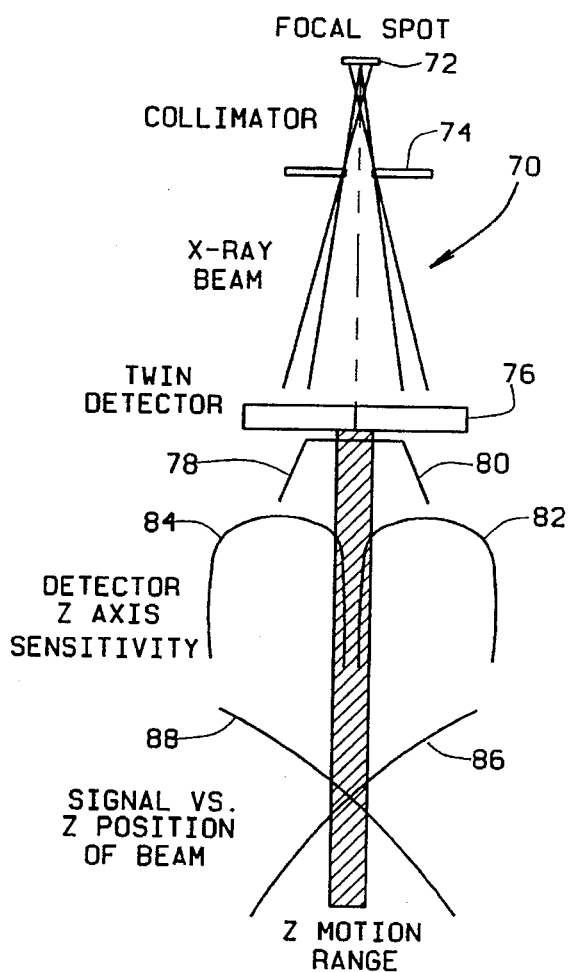
FIG. 4 schematically illustrates an x-ray beam and a two (or twin) detector cells, including the x-ray beam intensity profile, the z axis sensitivity of the cells, and the detector cell signals versus z axis position of the x-ray beam.

FIG. 4 illustrates a multi-slice (i.e., more than one row of detector cells) imaging system 70 including an x-ray being emitted from a focal spot 72. Beam 72 is collimated by a prepatient collimator 74 and impinges on a surface of detector cells 76 and 78. An x-ray beam intensity profile 80 and detector cell z axis sensitivity curves 82 and 84 are graphically shown below cells 76 and 78. In addition, detector cell signal versus z axis position of the x-ray beam curves 86 and 88 also are shown.

With multi-slice imaging system 70, and particularly from curves 82 and 84, it can be seen that calibration of the outputs from cells 76 and 78 is much less straightforward than in single slice system 50. Particularly, since the x-ray impinges on the edge regions of detector cells 76 and 78, and since the edge regions have a highly non-linear sensitivity (curves 82 and 84), the detector cell signal versus z axis position of the x-ray beam curves 86 and 88 are highly non-linear. Such non-linearities increase the difficulty in calibrating the detector cell outputs, especially for a thin slice x-ray beam.

The present invention, in one aspect, is a method for calibrating detector cell output in multi-slice systems. Such calibration is achieved without requiring the use of expensive precision post patient collimators so that the x-ray beam penumbra does not impinge on the detector cell edge regions. Rather, in one aspect, the present invention generates a ZCAL correction vector applicable for multi-slice systems.

More specifically, and in accordance with one embodiment of the present invention, the signal gain for each detector cell, or channel, at multiple z-axis locations is measured. The z-axis beam location is measured by a z-axis beam position sensor (or Z channel), such as, for example, the sensor described in copending U.S. patent application Ser. No. 08/576,066 Improved Z-Axis X-Ray Beam Position Sensor For Multi-Slice Computed Tomography, filed Dec. 21, 1995 (15-CT-4342) and assigned to the present assignee. The position sensor determines the beam position ($Z_r$) only at the Z channel location.

Figure 5:
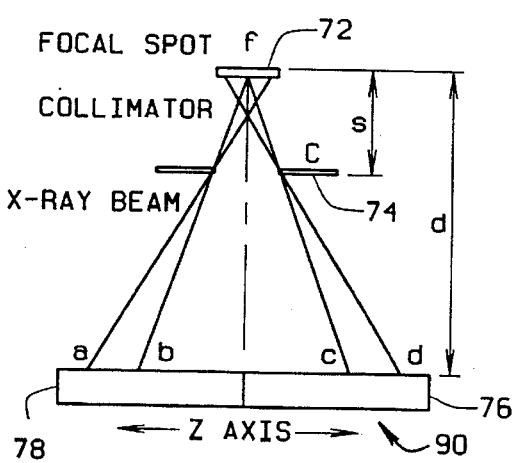
FIG. 5 schematically illustrates twin detector cells and x-ray beam z axis locations with respect to the cells.
Figure 6:
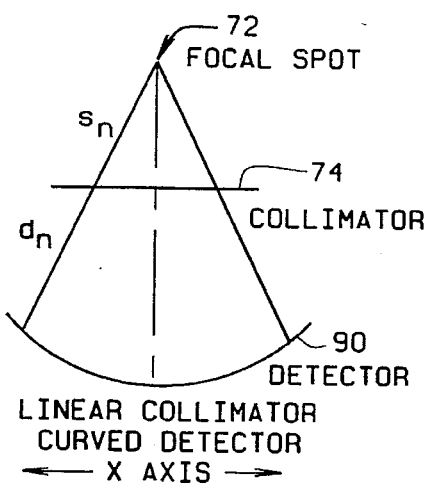
FIG. 6 illustrates a linear collimator and a curved detector cell array.
Figure 7:
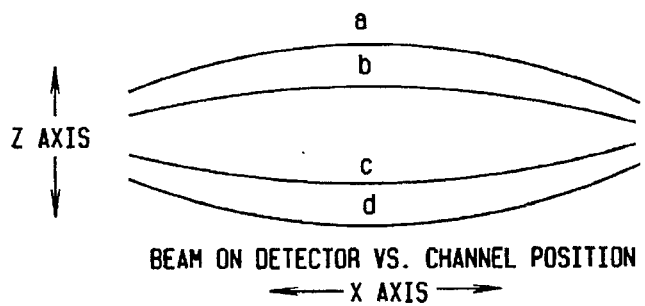
FIG. 7 illustrates the x-ray beam (center) location versus detector cell (or channel) position.

Referring to FIGS. 5, 6 and 7, each channel or detector cell 76 and 78 has a different X-ray beam position in the Z-axis that is dependent on the geometry of collimator 74, focal spot 72, and detector channel location in the fan beam. Detector 90, which includes detector cells 76 and 78, is curved as clearly shown in FIG. 6, and the z location ($Z_n$) is the point along the z-axis for each channel 76 and 78 where the x-ray beam is at FWHM intensity, as shown in FIG. 7.

To determine the signal, or gain, of each channel 76 and 78 at multiple z locations, collimator 74 is indexed through a set of z-axis positions during a calibration scan, for example, from −0.2 to +0.2 mm in 0.02 mm steps. Since the position of the focal spot changes as the tube heats, it is necessary to return collimator 74 to a reference location at the end of the calibration sequence to measure and correct for focal spot position change during calibration.

The z location ($Z_n$) for each channel 76 and 78 is related to the position of the focal spot as set forth below:

$$Z_n = (C-f)d_n/s_n + f \quad (1)$$

Z=position of beam on detector
f=position of focal spot in Z-axis
C=position of collimation point in Z-axis
d=detector to focal spot distance
s=source to collimation distance
n=channel index For each channel, a correction polynomial $Q_n$ is fitted to the signal variation curve as a function of z-axis position so that the correction polynomial value multiplied by its channel signal produces a constant value over the operational range of z-axis positions. The correction polynomial ($Q_n$) is:

$$Q_n = a_n + b_n Z_n + c_n Z_n^2 \quad (2)$$

$Q_n$ =reciprocal channel gain as a function of Z

Beam positions ($Z_r$) are measured as a function of each position reference signal ($D_r$) according to the equation:

$$Z_r = a_r + b_r D_r + c_r D_{r_n}^2 \quad (3)$$

$Z_r$=Z position at Z sensing channel as a function of the differential signal $D_r$ Accordingly, the Z position of the beam at the sensor channel is determined by Equation 3. The location of the focal spot is determined by:

$$f = \frac{\left(Z_r - C\dfrac{d_r}{s_r}\right)}{\left(1 - \dfrac{d_r}{s_r}\right)}, \quad (4)$$

where the position of the collimator, C, and the z-axis position of the beam for the reference channel $Z_r$ are known.

The z-axis location for each channel is then determined in accordance with Equation 1 and the ZCAL correction vector is determined in accordance with Equation 2. The ZCAL correction vector is then multiplied by the channel signal to calibrate the channel signal.

The ZCAL correction vector described above provides the important advantage that such vector can be used to calibrate channel signals in a multi-slice imaging systems, even in the presence of non-linearities due to the detector cell edge regions. Use of such ZCAL correction vector also eliminates use of costly precision post-patient collimators in a multi-slice imaging system.

With respect to CT systems for more than two slices (system 70 described above is a two-slice system), if the collimation system geometry permits a slight amount of penumbra to always fall on the outer detector rows over the operating z-axis motion range, then the signal variation versus z-axis beam position will be similar to the two-slice CT system beam curves. Thus, and in addition to being useful in two slice systems, the ZCAL correction algorithm described above may be used in a multi-slice CT system having more than two slices.

Figure 8:
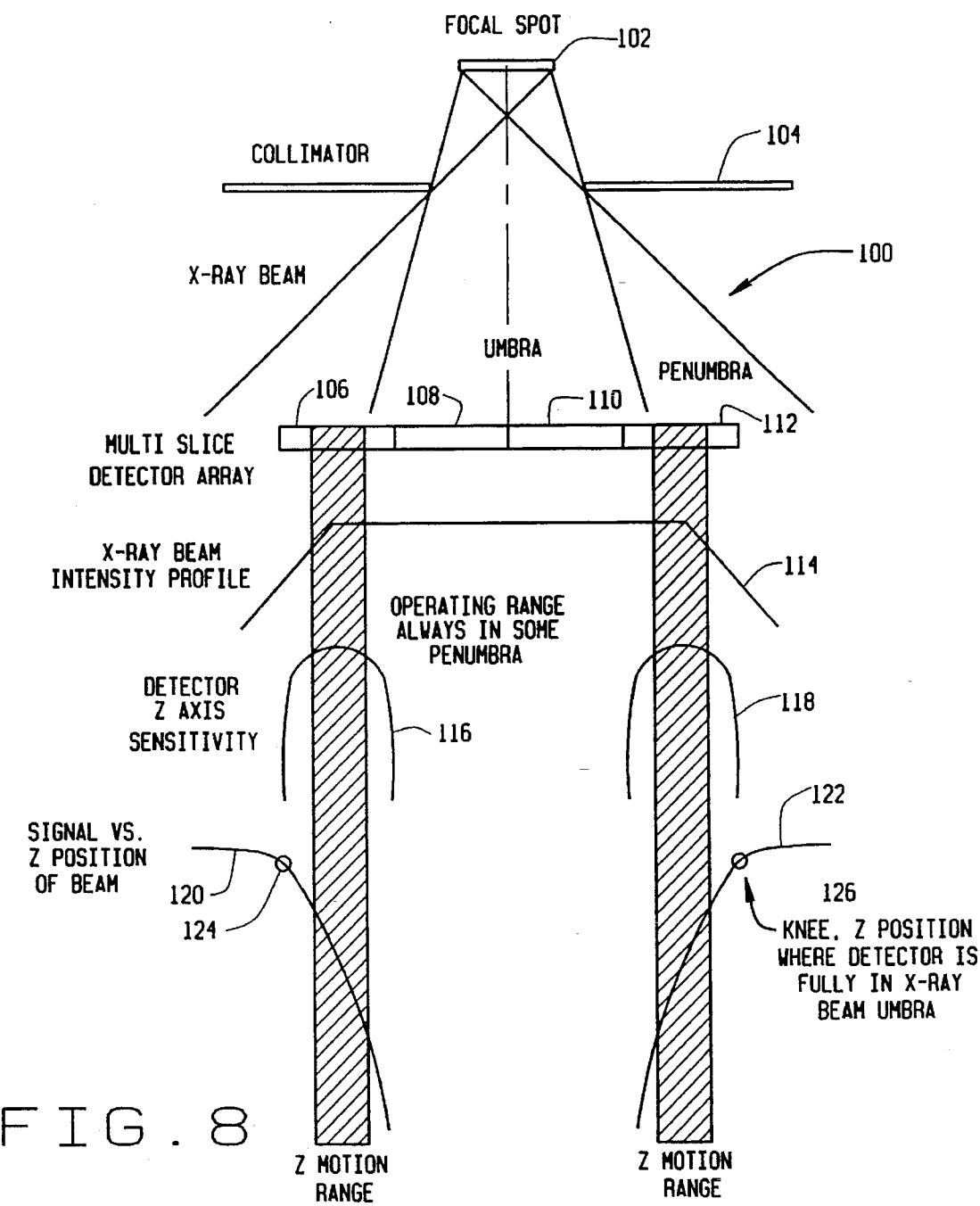
FIG. 8 schematically illustrates an x-ray beam and four detector cells, including the x-ray beam intensity profile, the z axis sensitivity of the outermost cells, and the outermost detector cell signals versus z axis position of the x-ray beam.

More specifically, FIG. 8 schematically illustrates a four-slice (i.e., imaging system 100 including an x-ray being emitted from a focal spot 102. The beam is collimated by a prepatient collimator 104 and impinges on a surface of detector cells 106, 108, 110 and 112. X-ray beam intensity profiles 114 and detector cell z axis sensitivity curves 116 and 118 for outermost cells 106 and 112 are graphically shown below cells 106 and 112. In addition, detector cell signal versus z axis position of the x-ray beam curves 120 and 122 also are shown.

As shown in FIG. 8, a slight amount of penumbra falls on outer detector cells 106 and 112 over the operating z-axis motion range. As a result, the signal variation versus z-axis beam position (curves 120 and 122) are similar to the two-slice CT system beam curves and the above described ZCAL correction can be used. However, if beam motion causes the penumbra to move off outermost detector cells 106 and 112, there will be a discontinuous point, or knee 124 and 126, where further movement causes virtually no change in signals from detectors 106 and 112. At this point, the detector array is fully flooded with umbra. Even a very high order function generally cannot define the sharp change in the shape of this curve accurately enough to avoid artifacts in a practical ZCAL correction vector implementation.

In such a situation, however, during calibration, the z-axis beam position of knee 124 and 126 can be identified as the first point above 0.99 times the maximum value on a seven point box car filtered set of signal versus beam position channel data. A polynomial correction function can then be fitted only to the curved portion up to and including the knee. The correction polynomial and z-axis position breakpoint are stored for each channel. During patient scanning, either the polynomial value or a constant correction is applied to each channel depending upon whether the beam position is above or below the knee.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the X-ray source and detector rotate with the gantry. Many other CT systems including "fourth generation" systems wherein the detector is a full-ring stationary detector and only the X-ray source rotates with the gantry, may be used. Accordingly, the spirit and scope of the invention are to be limited only by the terms of the appended claims.

What is claimed is:

1. A method for calibrating projection data in a multi-slice computed tomography system, the computed tomography system including an x-ray source and a detector array having at least two rows of detector cells, said method comprising the steps of:

determining the signal gain for each detector cell at multiple z-axis locations;

fitting a correction polynomial $Q_n$ to a signal variation curve as a function of z-axis position so that the correction polynomial value multiplied by its channel signal produces a constant value over the operational range of z-axis positions;

determining beam positions ($Z_r$) as a function of each position reference signal ($D_r$) and the Z position of the beam at a sensor channel;

determining a z-axis location for each detector cell and a correction vector for each cell; and multiplying each channel signal by the correction vector to calibrate each channel signal.

2. A method in accordance with claim 1 wherein in determining the signal gain for each detector cell at multiple z-axis locations is measured, the z-axis beam location is measured by a z-axis beam position sensor.

3. A method in accordance with claim 2 wherein the computed tomography system further includes a collimator and wherein in determining the signal gain of each channel at multiple z locations, the collimator is indexed through a set of z-axis positions during a calibration scan.

4. A method in accordance with claim 1 wherein the z location ($Z_n$) for each channel is related to the position of the x-ray source focal spot by:

$$Z_n = (C-f)d_n/S_n + f$$

where:

Z=position of beam on detector
f=position of focal spot in Z-axis
C=position of collimation point in Z-axis
d=detector to focal spot distance
s=source to collimation distance; and
n=channel index.

5. A method in accordance with claim 4 wherein the correction polynomial $Q_n$ is:

$$Q_n = a_n + b_n Z_n + c_n Z_n^2$$

where $Q_n$=reciprocal channel gain as a function of Z.

6. A method in accordance with claim 5 wherein beam positions ($Z_r$) are measured as a function of each position reference signal ($D_r$) according to the equation:

$$Z_r = a_r + b_r D_r + c_r D_{r_n}^2$$

where $Z_r$=Z position at Z sensing channel as a function of the differential signal $D_r$.

7. A method in accordance with claim 6 wherein the location of the focal spot is determined by:

$$f = \frac{\left(Z_r - C\frac{d_r}{s_r}\right)}{\left(1 - \frac{d_r}{s_r}\right)}.$$

8. A computer for a computed tomography system including an x-ray source and a detector array having at least two rows of detector cells, said computer configured to calibrate projection data and programmed to:

determine the signal gain for each detector cell at multiple z-axis locations;

fit a correction polynomial $Q_n$ to a signal variation curve as a function of z-axis position so that the correction polynomial value multiplied by its channel signal produces a constant value over the operational range of z-axis positions;

determine beam positions ($Z_r$) as a function of each position reference signal ($D_r$) and the Z position of the beam at a sensor channel;

determine a z-axis location for each detector cell and a correction vector for each cell; and multiply each channel signal by the correction vector to calibrate each channel signal.

9. A computer in accordance with claim 8 wherein in determining the signal gain for each detector cell at multiple z-axis locations is measured, the z-axis beam location is measured by a z-axis beam position sensor.

10. A computer in accordance with claim 9 wherein the computed tomography system further includes a collimator and wherein in determining the signal gain of each channel at multiple z locations, the collimator is indexed through a set of z-axis positions during a calibration scan.

11. A computer in accordance with claim 1 wherein the z location ($Z_n$) for each channel is related to the position of the x-ray source focal spot by:

$$Z_n = (C-f)d_n/S_n + f$$

where:

Z=position of beam on detector
f=position of focal spot in Z-axis
C=position of collimation point in Z-axis
d=detector to focal spot distance
s=source to collimation distance; and
n=channel index.

12. A computer in accordance with claim 11 wherein the correction polynomial $Q_n$ is:

$$Q_n = a_n + b_n Z_n + c_n Z_n^2$$

where $Q_n$=reciprocal channel gain as a function of Z.

13. A computer in accordance with claim 12 wherein beam positions ($Z_r$) are measured as a function of each position reference signal ($D_r$) according to the equation:

$$Z_r = a_r + b_r D_r + c_r D_{r_n}^2$$

where $Z_r$=Z position at Z sensing channel as a function of the differential signal $D_r$.

14. A computer in accordance with claim 13 wherein the location of the focal spot is determined by:

$$f = \frac{\left(Z_r - C\frac{d_r}{s_r}\right)}{\left(1 - \frac{d_r}{s_r}\right)}.$$

* * * * *